(12) United States Patent
Friedman et al.

(10) Patent No.: US 8,214,011 B2
(45) Date of Patent: Jul. 3, 2012

(54) SYSTEM AND METHOD FOR REMODELING PREDICTION USING ULTRASOUND

(75) Inventors: Zvi Friedman, Kiryat Bialik (IL); Peter Lysyansky, Haifa (IL); Dan Adam, Haifa (IL)

(73) Assignee: General Electric Company, Schenectady, NY (US)

( * ) Notice: Subject to any disclaimer, the term of this patent is extended or adjusted under 35 U.S.C. 154(b) by 826 days.

(21) Appl. No.: 12/190,947

(22) Filed: Aug. 13, 2008

(65) Prior Publication Data
US 2009/0048513 A1  Feb. 19, 2009

Related U.S. Application Data

(60) Provisional application No. 60/955,534, filed on Aug. 13, 2007.

(51) Int. Cl.
*A61B 5/05* (2006.01)
*A61B 8/00* (2006.01)
*G06K 9/00* (2006.01)

(52) U.S. Cl. ........ 600/407; 600/450; 600/451; 600/439; 382/128

(58) Field of Classification Search .................. 600/451, 600/439, 450; 382/128
See application file for complete search history.

(56) References Cited

U.S. PATENT DOCUMENTS

| | | | |
|---|---|---|---|
| 7,877,128 B2 * | 1/2011 | Schwartz | 600/407 |
| 7,912,270 B2 * | 3/2011 | Skinner et al. | 382/131 |
| 2004/0153128 A1 * | 8/2004 | Suresh et al. | 607/14 |

* cited by examiner

*Primary Examiner* — Long V. Le
*Assistant Examiner* — Helene Bor
(74) *Attorney, Agent, or Firm* — The Small Patent Law Group; Dean D. Small

(57) ABSTRACT

A system and method for remodeling prediction using ultrasound are provided. The method includes obtaining ultrasound information relating to a heart and determining a likelihood of myocardial remodeling of the heart based on the ultrasound information.

22 Claims, 10 Drawing Sheets

SYSTEM AND METHOD FOR REMODELING PREDICTION USING ULTRASOUND

CROSS REFERENCE TO RELATED APPLICATIONS

This application claims priority to and the benefit of the filing date of U.S. Provisional Application No. 60/955,534 filed Aug. 13, 2007 for "MEASURES SENSITIVE TO MYOCARDIAL FUNCTION AND POST-AMI REMODELING", which is hereby incorporated by reference herein in its entirety.

BACKGROUND OF THE INVENTION

Embodiments of the present invention relate generally to medical imaging systems, and more particularly, to ultrasound imaging systems, especially for cardiac imaging.

Cardiac remodeling (CR), also referred to a ventricular remodeling, is the change in the size, shape and/or function of the heart, which can occur after injury to the left ventricle. The injury most commonly results from acute myocardial infarction (AMI), which is usually transmural, and evidenced as ST segment elevation in the ECG waveform. However, AMI generally causes regional decrease of myocardial function in the region suffering from lack of blood supply, which results in increased work demand from the remaining regions of the heart.

CR is a process that involves changes of the myocardial tissue properties (e.g. contractility) and is accompanied by an increase in the myocardial mass and in particular left ventricular (LV) mass and volume, as well as a change in the shape of the ventricle that eventually leads to congestive heart failure (CHF). Thus, as more people survive AMI, more people are potentially at risk of CHF. Post-AMI remodeling is asymmetric and is initially triggered and associated with infarct expansion. Infarct expansion, which is related to work performed by myocytes that do not receive enough blood supply (ischemic), occurs mostly through apoptosis (programmed cell death).

Known clinical practices to determine remodeling indices are based on serial follow-ups to measure global functional parameters, for example, ejection fraction and LV volumes. The follow-up and monitoring of these indices are commonly used as indices of success of a particular therapy (e.g., administered medications). These global indices are, however, of low sensitivity. Specifically, these indices are of very low sensitivity to cardiac changes occurring post-AMI, and to regional changes, which actually initiate the cascade of events eventually leading to heart failure.

One known system for assessing cardiac remodeling uses cardiac tagged-MRI. However, the system is extremely expensive and of limited availability. In ultrasound imaging, there are no quantitative measures of regional myocardial function (even among those based on echo-ultrasound speckle tracking). Current clinical ultrasound methods only allow quantification of the function of the whole 2D/3D volume of the myocardium. Additionally, no quantitative ultrasound measures of myocardial remodeling exist. Accordingly, there is no efficient indication that may guide a cardiologist with respect to how to slow or reverse the remodeling process.

BRIEF DESCRIPTION OF THE INVENTION

In accordance with an embodiment of the present invention, a method for determining a likelihood of myocardial remodeling is provided. The method includes obtaining ultrasound information relating to a heart and determining a likelihood of myocardial remodeling of the heart based on the ultrasound information.

In accordance with another embodiment of the present invention, a method for determining a likelihood of myocardial remodeling is provided. The method includes determining a plurality of strain curves over time based on ultrasound information of a heart and determining an amount of local work for each point in the left ventricle of the heart, based on the strain curves. The method further includes generating a remodeling map based on the determined amount of local work and determining a likelihood of regional myocardial remodeling based on the remodeling map.

In accordance with yet another embodiment of the present invention, an ultrasound system is provided that includes a transducer configured to acquire ultrasound information of a heart. The ultrasound system further includes a processor module configured to determine a likelihood of myocardial remodeling of the heart based on the ultrasound information.

DETAILED DESCRIPTION OF THE INVENTION

Figure 1:
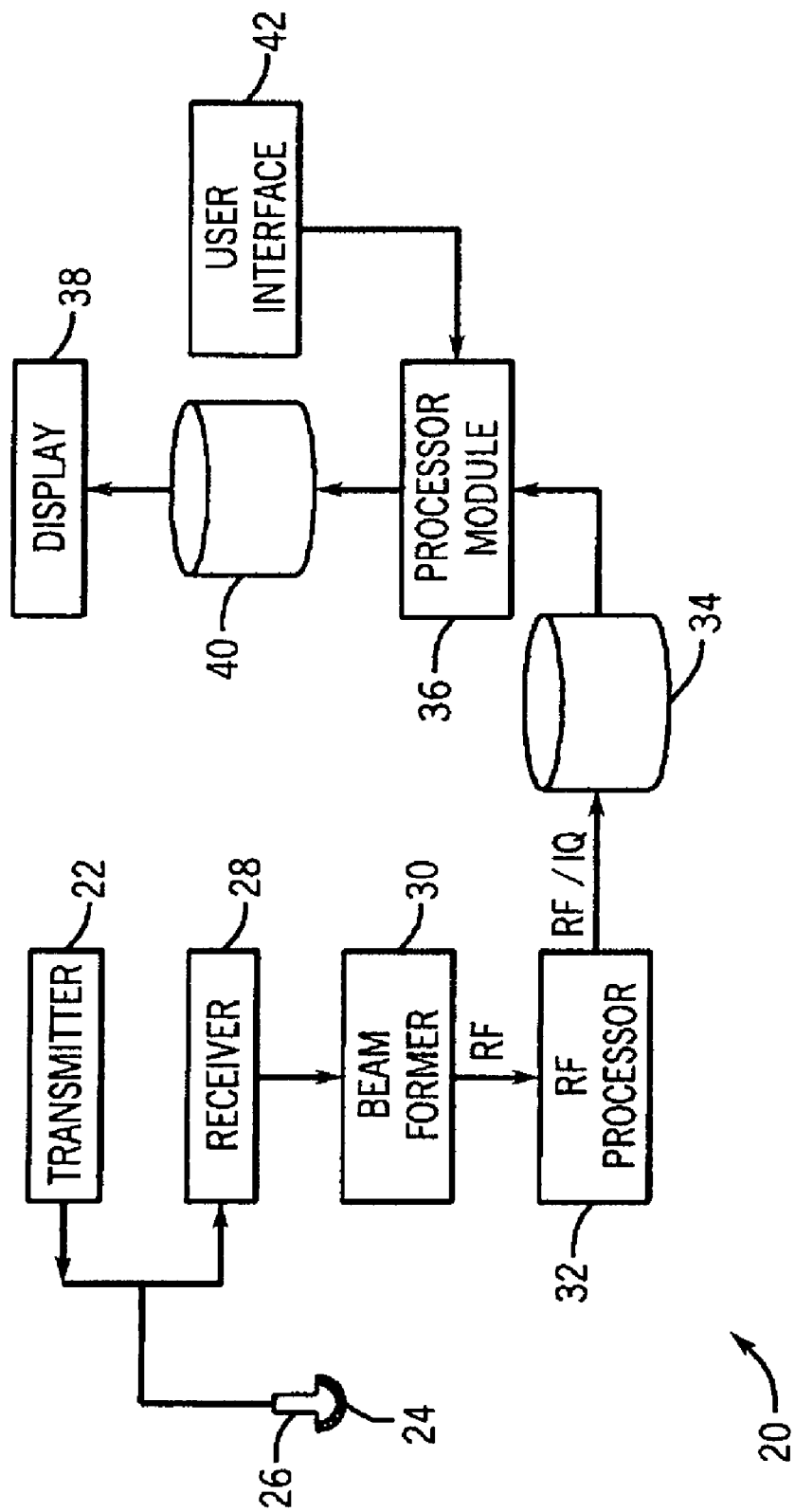
FIG. 1 is a block diagram of a diagnostic ultrasound system configured to determine a probability of remodeling in accordance with various embodiments of the invention.

The foregoing summary, as well as the following detailed description of certain embodiments of the invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of ultrasound systems and methods for predicting cardiac remodeling using local indices based on regional measurements are described in detail below. In particular, a detailed description of an exemplary ultrasound system will first be provided followed by a detailed description of various embodiments of methods and systems for predicting cardiac remodeling.

At least one technical effect of the various embodiments of the systems and methods described herein include determining a likelihood or predicting cardiac remodeling using local indices based on regional measurements from an ultrasound system. The parameters used to predict cardiac remodeling and infarct expansion allow for optimizing of preventative treatments. For example, the prediction of remodeling supports cardiologists attempting to treat the post-AMI patient and minimize deterioration to CHF.

It should be noted that although the various embodiments may be described in connection with an ultrasound system, the methods and systems described herein are not limited to ultrasound imaging or a particular configuration thereof. In particular, the various embodiments may be implemented in connection with different types of medical imaging, including, for example, magnetic resonance imaging (MRI) and computed-tomography (CT) imaging. Further, the various embodiments may be implemented in other non-medical imaging systems, for example, non-destructive testing systems.

FIG. 1 is a block diagram of an ultrasound system 20, and more particularly, a diagnostic ultrasound system formed in accordance with an embodiment of the present invention that may be used to perform ultrasound imaging as described in more detail below to predict cardiac remodeling. The ultrasound system 20 includes a transmitter 22 that drives an array of elements 24 (e.g., piezoelectric crystals) within a transducer 26 to emit pulsed ultrasonic signals into a body or volume. A variety of geometries may be used and the transducer 26 may be provided as part of, for example, different types of ultrasound probes. The ultrasonic signals are back-scattered from structures in the body, for example, blood cells or muscular tissue, to produce echoes that return to the elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis and analysis. The display 38 may automatically display, for example, a map showing predictors of regional cardiac remodeling based on, for example, a three-dimensional (3D) ultrasound data set stored in the memory 34 or 40. One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the ultrasound system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data is acquired by holding the transducer 26, or moving the transducer 26 such as along a linear or arcuate path, while scanning a region of interest (ROI), which may be moved manually, mechanically or electronically, or a combination thereof. At each linear or arcuate position, the transducer 26 obtains scan planes that are stored in the memory 34.

Figure 2:
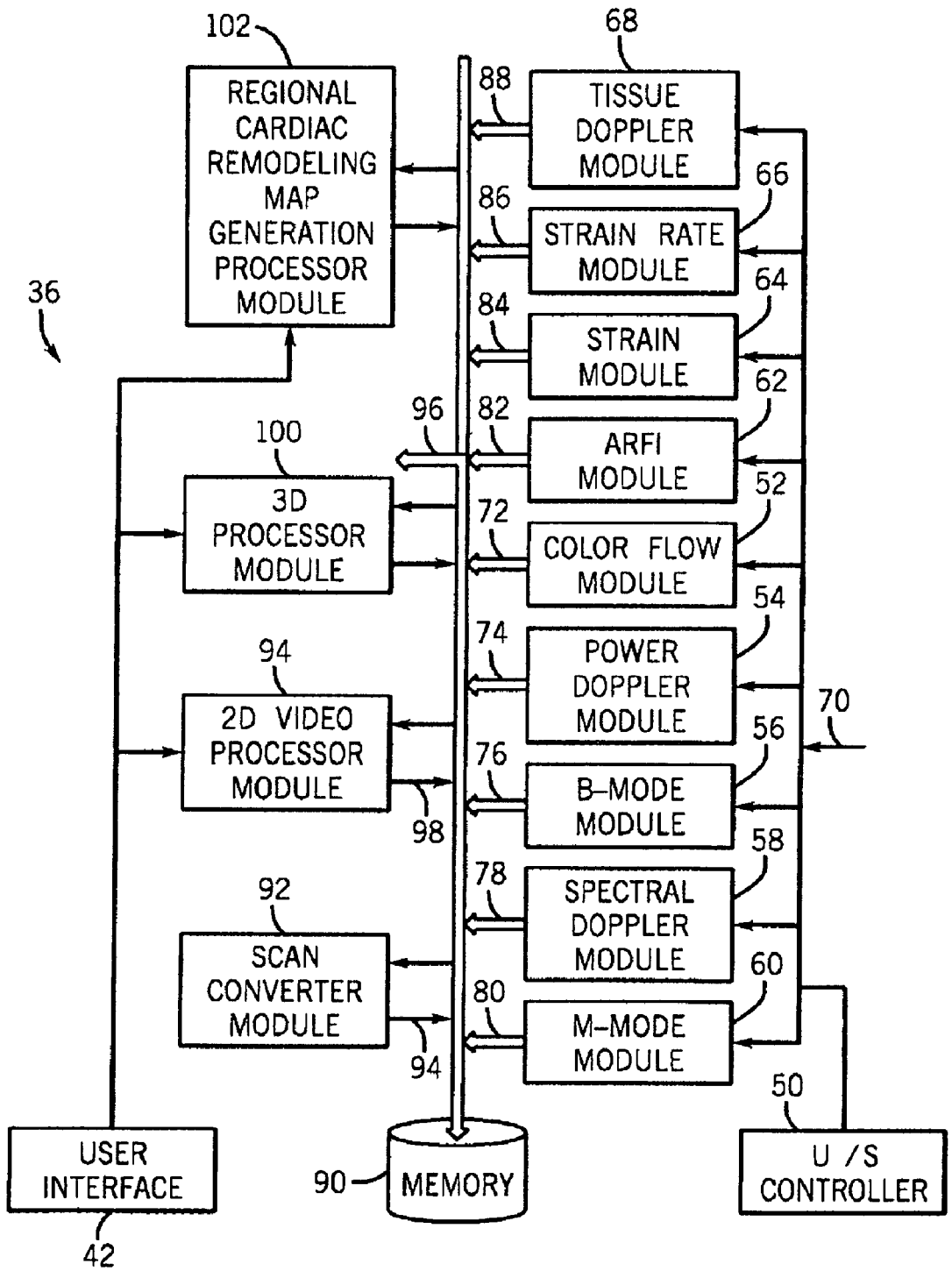
FIG. 2 is a block diagram of an ultrasound processor module of the diagnostic ultrasound system of FIG. 1 formed in accordance with an embodiment of the invention.

FIG. 2 illustrates an exemplary block diagram of the ultrasound processor module 36 of FIG. 1 formed in accordance with an embodiment of the present invention. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-68 perform mid-processor operations. The ultrasound processor module 36 may receive ultrasound data 70 in one of several forms. In the embodiment of FIG. 2, the received ultrasound data 70 constitutes I,Q data pairs representing the real and imaginary components associated with each data sample. The I,Q data pairs are provided to one or more of a color-flow sub-module 52, a power Doppler sub-module 54, a B-mode sub-module 56, a spectral Doppler sub-module 58 and an M-mode sub-module 60. Optionally, other sub-modules may be included such as an Acoustic Radiation Force Impulse (ARFI) sub-module 62, a strain module 64, a strain rate sub-module 66, a Tissue Doppler (TDE) sub-module 68, among others. The strain sub-module 62, strain rate sub-module 66 and TDE sub-module 68 together may define an echocardiographic processing portion.

Each of sub-modules 52-68 are configured to process the I,Q data pairs in a corresponding manner to generate color-flow data 72, power Doppler data 74, B-mode data 76, spectral Doppler data 78, M-mode data 80, ARFI data 82, echocardiographic strain data 84, echocardiographic strain rate data 86 and tissue Doppler data 88, all of which may be stored in a memory 90 (or memory 34 or image memory 40 shown in FIG. 1) temporarily before subsequent processing. The data 72-88 may be stored, for example, as sets of vector data values, where each set defines an individual ultrasound image frame. The vector data values are generally organized based on the polar coordinate system.

A scan converter sub-module 92 access and obtains from the memory 90 the vector data values associated with an image frame and converts the set of vector data values to Cartesian coordinates to generate an ultrasound image frame 95 formatted for display. The ultrasound image frames 95 generated by the scan converter module 92 may be provided back to the memory 90 for subsequent processing or may be provided to the memory 34 or the image memory 40.

Once the scan converter sub-module 92 generates the ultrasound image frames 95 associated with, for example, the strain data, strain rate data, and the like, the image frames may be restored in the memory 90 or communicated over a bus 96 to a database (not shown), the memory 34, the image memory 40 and/or to other processors, for example, the regional cardiac remodeling map generation processor module 102.

As an example, it may be desired to view different types of ultrasound images or associated data (e.g., strain curves or traces) relating to echocardiographic functions in real-time on the display 38 (shown in FIG. 1). To do so, the scan converter sub-module 92 obtains strain or strain rate vector data sets for images stored in the memory 90. The vector data is interpolated where necessary and converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 38, which may include one or more monitors or windows of the display, to display the image frame. The echocardiographic image displayed in the display 38 is produced from an image frame of data in which each datum indicates the intensity or brightness of a respective pixel in the display. In this example, the display image represents muscle motion in a region of interest being imaged and may include a predicted remodeling value are described in more detail herein.

Referring again to FIG. 2, a 2D video processor sub-module 94 combines one or more of the frames generated from the different types of ultrasound information. For example, the 2D video processor sub-module 94 may combine a different image frames by mapping one type of data to a grey map and mapping the other type of data to a color map for video display. In the final displayed image, the color pixel data is superimposed on the grey scale pixel data to form a single multi-mode image frame 98 that is again re-stored in the memory 90 or communicated over the bus 96. Successive frames of images may be stored as a cine loop in the memory 90 or memory 40 (shown in FIG. 1). The cine loop represents a first in, first out circular image buffer to capture image data that is displayed in real-time to the user. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three dimensional image representations thereof, such as through volume rendering or surface rendering algorithms as are known. The three dimensional images may be generated utilizing various imaging techniques, such as ray-casting, maximum intensity pixel projection and the like.

The regional cardiac remodeling map generation processor module 102 is also controlled by the user interface 42 and accesses the memory 90 to obtain ultrasound information, and as described in more detail below, use ultrasound strain data to generate a map of the strain, which in the various embodiments is used to determine local indices of the left ventricle over time. From the local indices, a local work function may be calculated as described herein to thereby generate a cardiac map providing regional predictors of cardiac remodeling.

More particularly, cardiac remodeling mapping in accordance with various embodiments may provide assessment of early ventricular remodeling following coronary occlusion that is triggered (and dominated by) and may cause infarct expansion. Ventricular remodeling is initiated by and causes infarct expansion within the akinetic-hypokinetic segments adjacent to the infracted area followed by mainly volume-overload hypertrophy of the non-infarcted segments. Further volume enlargement, a lengthening of the ventricular perimeters, and an increased sphericity index both in systole and diastole is accompanied by a blunting of the normal curvature of the apex. Thereafter, what is usually called remodeling is characterized by additional enlargement and sphericity of the ventricle, a decrease in stroke volume, and impaired diastolic filling. Based in part on one or more of these factors, the various embodiments provide a model of ventricular remodeling after myocardial infarction based on a cascade of the following events: systolic impairment secondary to the continuous loss of contractile material, resulting in an increased end-systolic volume, an increased cardiac size, and a secondary augmentation of the diastolic filling pressure and cardiac distensibility. As the fibrosis increases, the tissue distensibility decreases, resulting in a further increase in diastolic pressure and volume. Peripheral mechanisms including vasoconstriction subsequently increase both preload and afterload, which results in an increased wall stress and a progressive thinning of the area. Simultaneously, in the noninfracted segments, elevation of the end-diastolic stress causes volume-overload hypertrophy that tends to normalize the wall stress according to Laplace's law. Using mapping in accordance with various embodiments, the extent and location of the infarction, therapy, or associated diseases may be provided to modify cardiac remodeling by, for example, therapeutic means.

It should be noted that cardiac remodeling often also originates from a more general process such as arterial hypertension or valvular disease, in which case the ventricular hypertrophy remains symmetric. Compensated cardiac hypertrophy (CCH) is concentric and is initially characterized by a thick ventricular wall and septum, a normal internal volume and wall stress, and a high mass-to-volume ratio. Cardiac failure (CF) occurs when the normal compensation fails, and instead of increased contractile efficiency the myocardium develops more connective tissue, which is accompanied by a progressive enlargement of the ventricular cavity, and the mass-to-volume ratio returns to normal values. Various embodiments of the invention are not necessarily, but may be directed to this type of remodeling.

Figure 3:
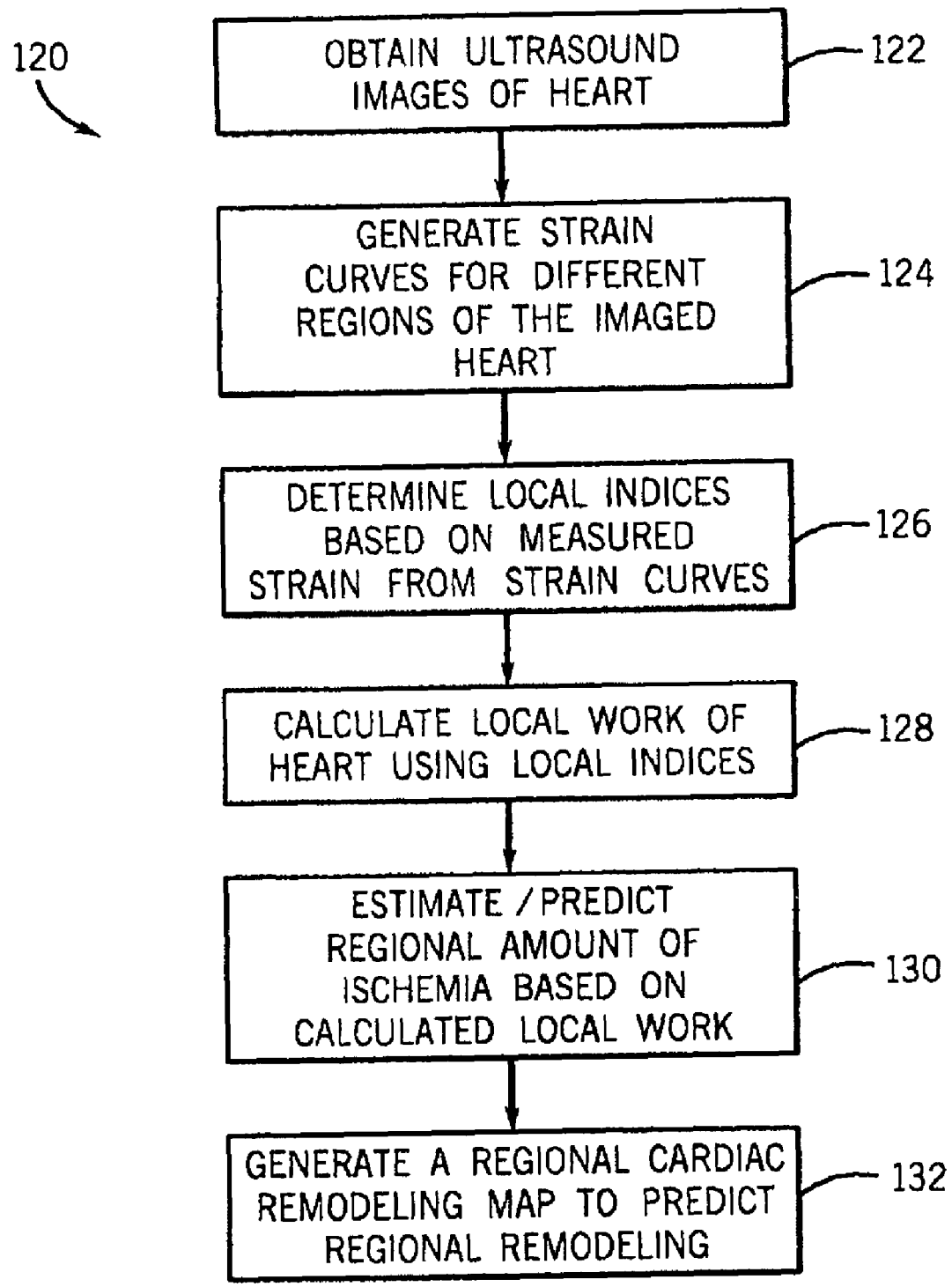
FIG. 3 is a flowchart of a method for generating a regional cardiac remodeling map to predict regional remodeling in accordance with various embodiments of the invention.

A method 120 for generating a regional cardiac remodeling map to predict regional remodeling is shown in FIG. 3. The method 120 includes obtaining ultrasound images of a heart at 122. For example, different views of a heart may be acquired by the ultrasound system 20 (shown in FIG. 1) using any know scanning process. The different views of the heart may include three standard views as is known, which include an apical long axis (APLAX) view, a two-chamber (2-chamber) view and a four-chamber (4-chamber) view. Multiple standard views of the heart may be acquired, for example, at different times during a heart cycle.

One or more strain curves for different regions of the imaged heart then may be generated at 124 using any known process. It should be noted that when reference is made herein to a region of the heart, this may refer to a local area of the heart, such as a portion of the base, apex, etc. of the myocardium and corresponds, for example, to an area or point of the heart, which may be about one square centimeter (1 cm²). In others embodiments, and for example, this area may be as small as 0.2 millimeters (mm)×0.2 mm. The strain curves may be based on a measure of local instantaneous strain value as a function of time. For example, the local instantaneous strain value may be a percentage value based on a change in length of the heart muscle at a particular local location, such as based on a percent of muscle contraction. The strain value may be calculated in any known manner using, for example, the strain module 64 (shown in FIG. 2), operating in a manner based on any known process or method. The calculated strain values may be stored in a database that associates the strain value with a portion of the ultrasound image and corresponding, for example, to a pixel position or location of the imaged heart. The stored strain values may be, for example, the peak systolic value, which in one embodiment is the peak systolic strain, and more particularly, the peak negative strain if the peak occurs during systole or end systolic strain if the peak occurs later. This value generally may be the strain value for any local portion of, for example, the left ventricle of the heart, as a function of any time period during one or more heart cycles.

Using the measured stain values from the strain curves, local indices are thereafter calculated at 126. In particular, one or more local indices may be calculated that generally define remodeling related parameters. The one or more indices generally relate to work performed in ischemic, overloaded (mainly afterloaded) regions of the heart and define parameters that relate to the amount of ischemia and afterload of that region, as well as the work performed by that region (e.g., amount of muscle contraction or blood forced through that region).

For example, a post-systolic shortening index (PSSI) that defines ischemia/afterload, may be defined and calculated. Specifically, for each region or segment of the heart, the variable post-systolic shortening index (as the percent change in length (% ΔL)), is calculated as follows:

$$PostSystolicShorteningIndex = \frac{(\text{End-diastolic length} - \text{minimal segment length})}{(\text{End-diastolic length})} \times 100$$

As another example, an index of segmental work (SW) may be calculated which determines the local work of the heart at 128. It should be noted that local stress is related to ventricular pressure, whereas local strain can be measured by 2D Strain (as described herein). It also should be noted that in the calculation of this index, ventricular pressure is related to a weighted percentage of recruited myocytes. Accordingly, the segmental work (e.g., mechanical function of the heart at one segment) of the point k $SW_k$ is calculated as follows:

$$SW_k = L_0(k) \int_{Start\ Recruitment}^{End\ Recruitment} PercentRecruitment(t) \times Strain_k(t)\, dt$$

Where:
$L_0(k)$ is the local length at the start of systole;
StartRecruitment is the time when zones start to be recruited (start on contraction);
EndRecruitment is the time when all zones are released;
PercentRecruitment(t) is the percent of segments recruited at the time t;
$Strain_k(t)$ is the strain at the zone k at the time t.

Figure 4:
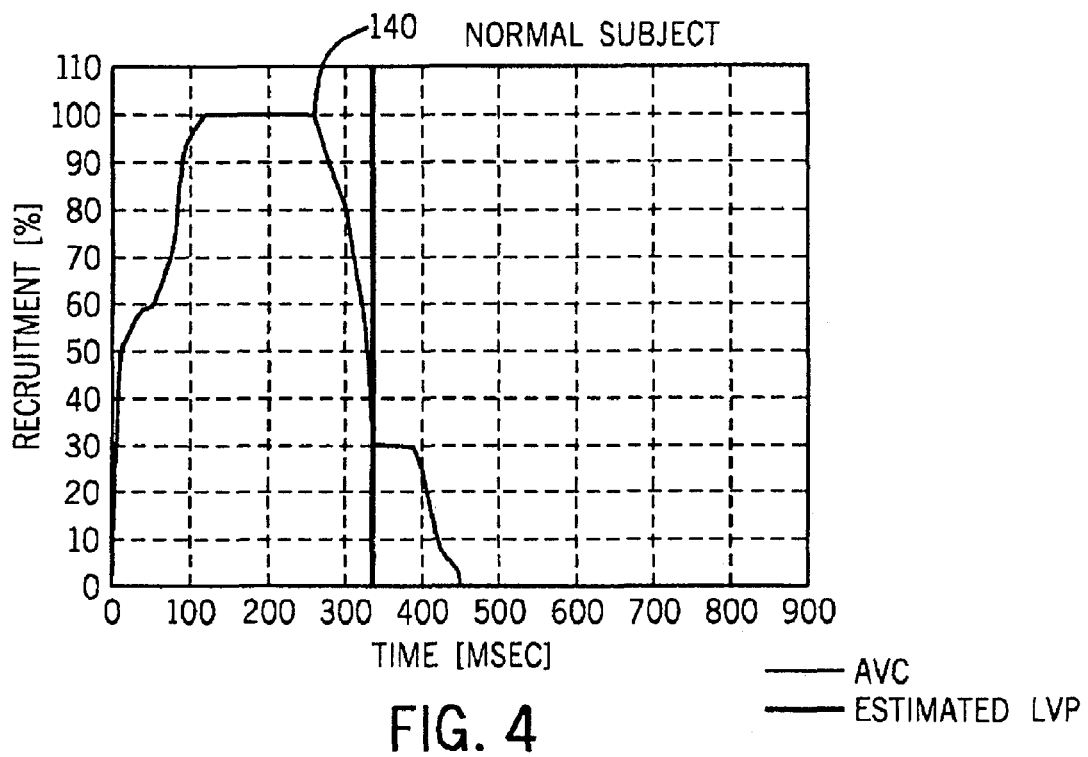
FIG. 4 is a graph illustrating recruitment in a normal individual, in relationship to the Aortic Valve Closure time.
Figure 5:
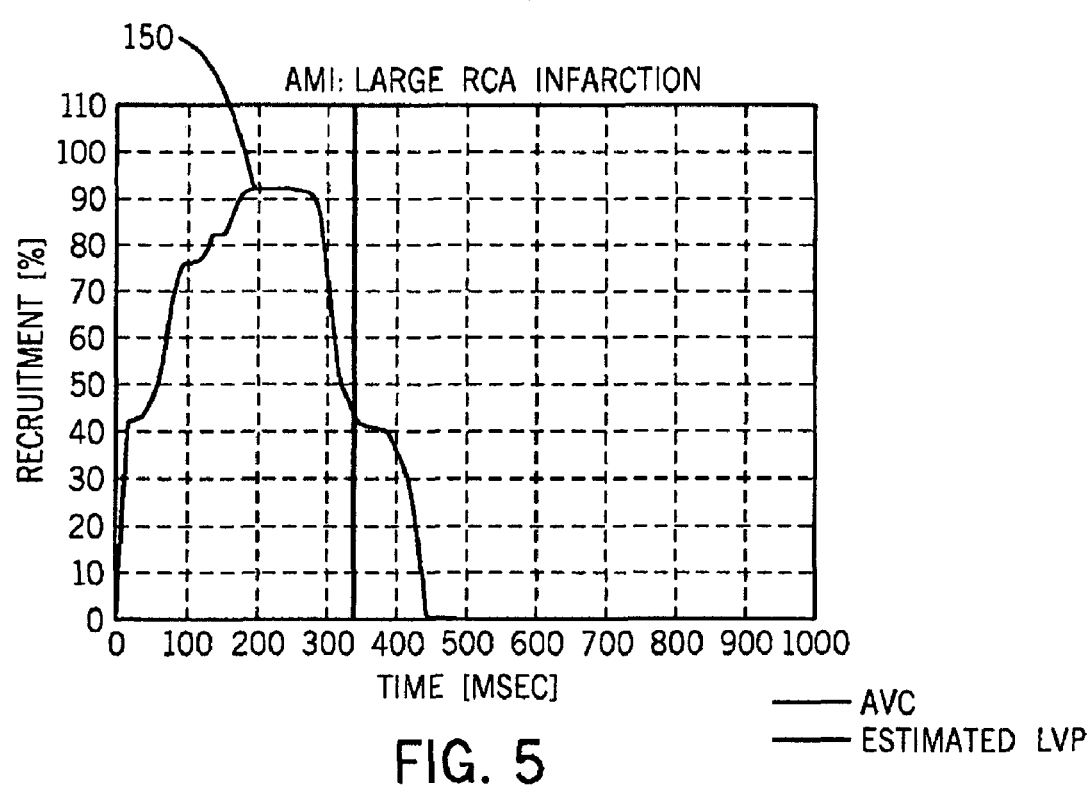
FIG. 5 is a graph illustrating recruitment in an acute myocardial infarction (AMI) individual, in relationship to the Aortic Valve Closure time.

It should be noted that zones generally refer to local areas or regions of the heart. Also, as shown in FIGS. 4 and 5, the recruitment (pressure surrogate) in a normal individual and an AMI individual are illustrated by the curves 140 and 150, respectively. As can be seen, there is a slight decrease in recruitment and de-recruitment rates, similar to the decrease in positive and negative dP/dt from such normal to AMI individuals.

In various embodiments, the local work performed by the heart is defined by the index of SW as described above. Specifically, the value of the local work at each point or region of the heart is the value of the index at that point or region.

A remodeling index (RI), for example, in acute infarction patients also may be calculated. It should be noted an acute myocardial infarction usually results in an infarcted area, mostly diskinetic or akinetic, surrounded with a hypokinetic ischemic area, referred to as "area at risk". The infarcted (diskinetic or akinetic) zone will then expand into the "area at risk", because myocytes in the area at risk are stimulated to generate work under conditions of ischemia and increased "afterload". Under these conditions both contraction and relaxation become slow. The increased afterload results because the remote non-ischemic myocytes are faster to contract and exert force on the slower ischemic myocytes. In one embodiment, areas that produce work, yet do not receive enough blood supply (ischemic) as described above, are determined to likely undergo myocyte death, which is mostly apoptosis. Accordingly, the ischemic "at risk" area around an infarction is determined in the strain map based on "post systolic" activity as described herein.

Moreover, cell death (e.g., myocytes apoptosis) is related to the workload on the area at risk and prognosis is related to the size of the area at risk. Accordingly, the RI is defined as the product of the local work and an index i, which defines post systolic activity, for example, as follows:

$$i = \begin{Bmatrix} 1(PSSI > 0.2) \\ 0(PSSI < 0.2) \end{Bmatrix}$$

The remodeling Index (RI) will thus be defined as:

$$RI = i \times \text{LocalWork}$$

It should be noted that that value of i may be varied, for example, based on the particular patient.

Figure 6:
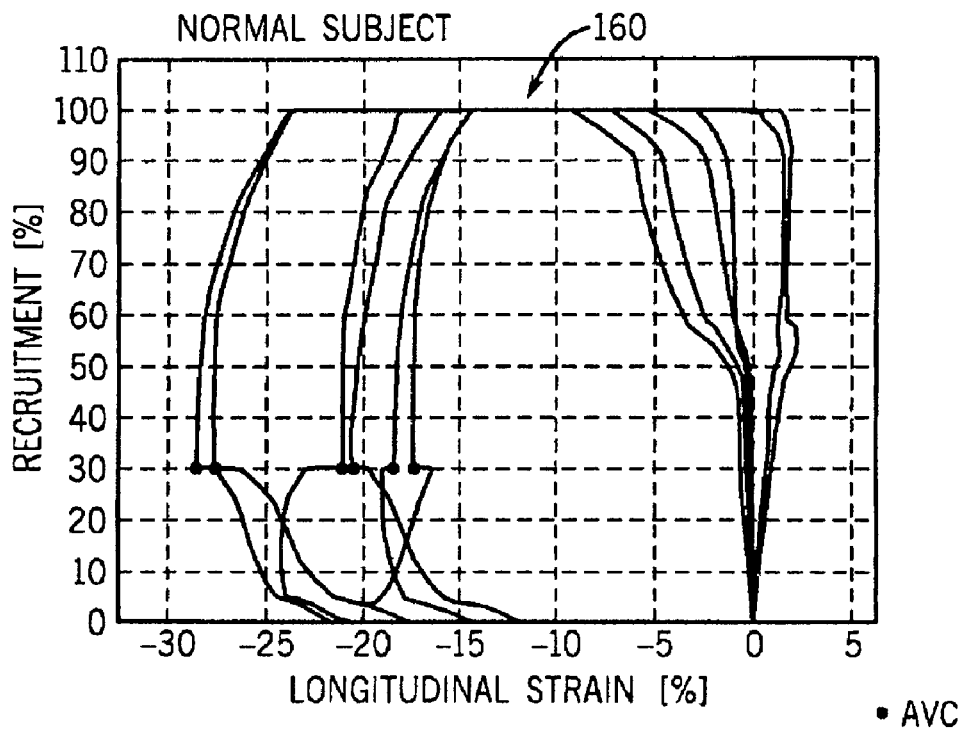
FIG. 6 is a graph illustrating regional work in a normal individual, calculated by plotting the percent recruitment versus the longitudinal strain (in percent).
Figure 7:
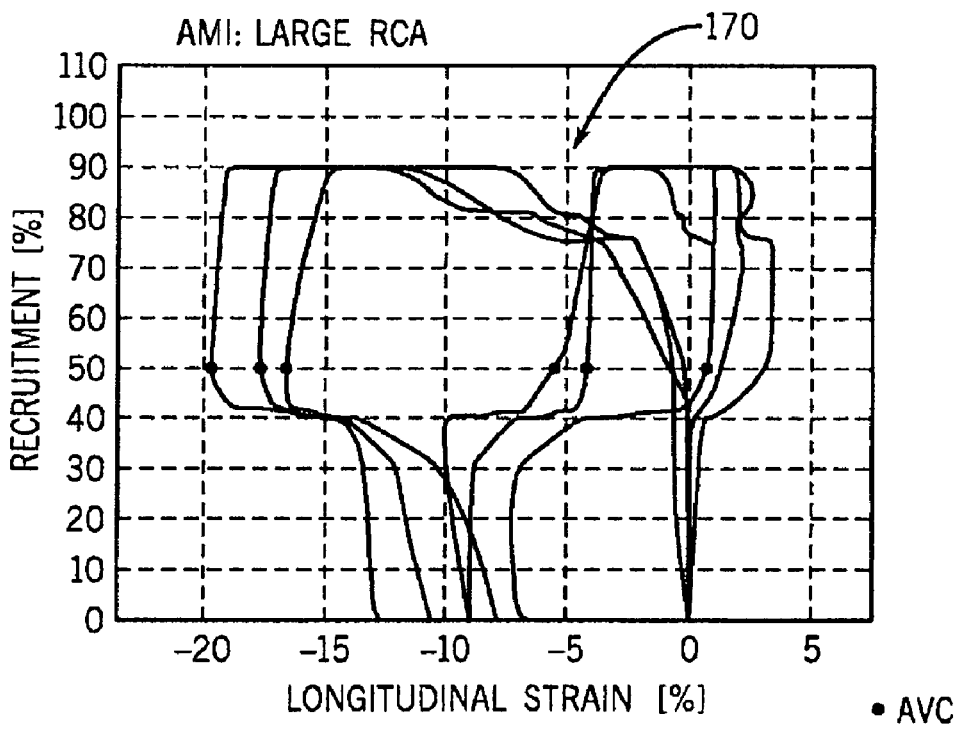
FIG. 7 is a graph illustrating regional work in an acute myocardial infarction (AMI) individual, calculated by plotting the percent recruitment versus the longitudinal strain (in percent).

Thus, using the RI, at 130 the regional amount of ischemia based on calculated local work may be estimated. For example, a remodeling index may be calculated for each of a plurality of local regions of the left ventricle, the values of which are the likelihood of myocardial remodeling. As described herein, the first event in the "remodeling cascade" is infarct expansion due to cell death, which is mainly apoptosis in the area at risk. Thus, the various embodiments relate the probability of cell death to the work performed in the ischemic/overloaded region with a resultant infarct expansion (and other processes described above). Apoptosis is caused due to work demand without appropriate blood/oxygen supply, or with elevated afterload. For example, as shown in FIGS. 6 and 7 the regional work in a normal individual and an AMI individual are illustrated by the curves 160 and 170, respectively. As can be seen, there is a noticeable change in the local P-V loops equivalence in the infarcted regions.

Thus, and for example, the "weighted percent recruitment" (WPR) (the number of LV regions, ~150/LV, which have started contraction, but have not yet reached relaxation) during systole strongly resembles the functional form of the systolic pressure curve. WPR curves can be derived from a plurality (~150/LV) of strain curves or traces obtained echocardiographically, for example, in the three standard apical views (4-chamber, 2-chamber and APLAX) in normal individuals as well as in various groups of individuals: LAD, RCA, LSX myocardial infarction and CHF individuals. WPR is generally defined as a weighted sum of loci that were in a contractile phase. The start of contraction is determined by the time when the strain trace starts to decline. The end of contraction is determined as the time when the strain curve reaches minimum. Maximum WPR during systole, $\tau$ of systolic WPR relaxation, and maximum diastolic re-recruitment (MDRR), are also measured.

In some embodiments, the maximum WRP is 100% in normal individuals and the following in individuals having heart injury: 80±17% (LAD), 72±11% (RCA), 93±8% (LCX) and 74±20% in CHF patients. Moreover, $\tau$ of systolic WPR relaxation in some embodiments are as follows:

|  | Normal | LAD | RCA | LCX | CHF |
| --- | --- | --- | --- | --- | --- |
| Average | 30.4 | 52.6 | 20.0 | 30.0 | 49.3 |
| STDV | 6.7 | 7.9 | 2.2 | 12.9 | 14.4 |

It should be noted that CHF individuals may have significant post-systolic activity, with an MDRR of 41±25%.

Thus, WPR curves are significantly different between normal individuals and individuals with heart injury, as well as among the various type of pathologies in different AMI subgroups and CHF patients. Specifically, the $\tau$ parameter may point to apical dysfunction, probably reduced de-rotation rate, whereas the MDRR could be an index related to marked inhibition of the $Ca^{+2}$ reuptake by the sarcoplasmic reticulum.

Figure 8:
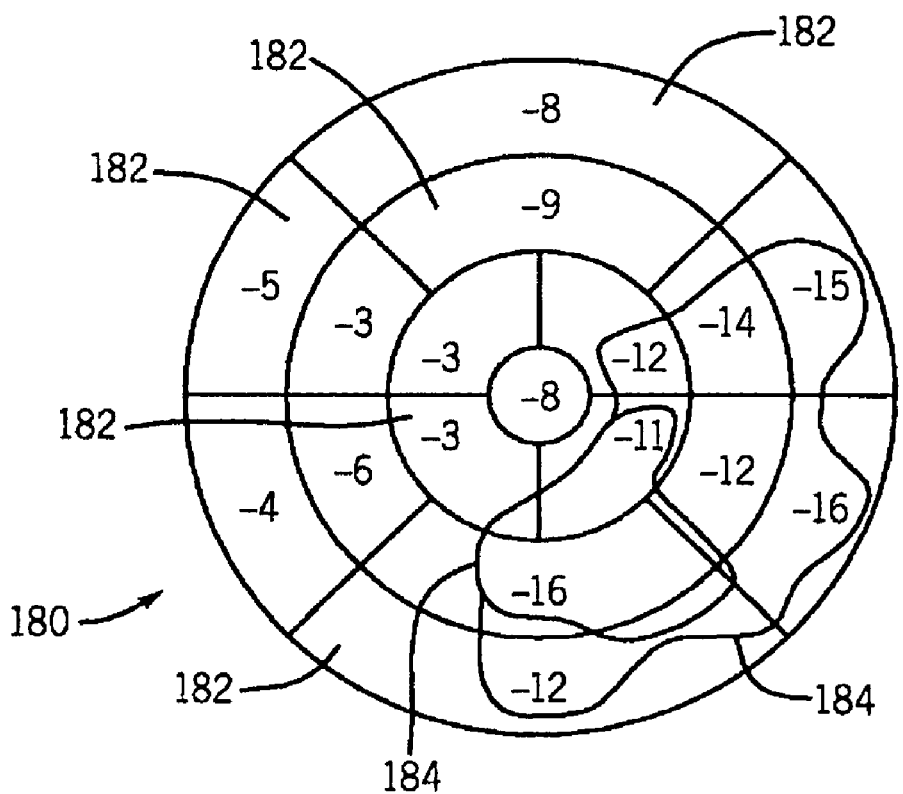
FIG. 8 is bullseye plot formed in accordance with various embodiments of the invention.

Referring again to the method 120 shown in FIG. 3, after estimating or predicting the regional amount of ischemia based on calculated local work, a regional cardiac remodeling map may be generated at 132 that shows the probability of remodeling in local regions of the heart, such as the left ventricle (e.g., predicting the likelihood of myocardial remodeling). For example, as shown in FIG. 8, the map may be a bullseye plot 180 having a plurality of segments 182 as is known (17 segments are shown, but more or less segments, for example, 16 segments or 18 segments may be provided). Each of the segments 182 may include therein a numeric value indicating the peak systolic strain for that segment 182. Additionally, regions 184 indicative of possible remodeling as determined by the RI may be provided and in some embodiments are color coded to identify the probability or likelihood of remodeling. For example, dark red may indicate a local region or area at high risk for remodeling, light red may indicate a local region or area at moderate risk for remodeling and blue may indicate a local region or area at very low risk for remodeling. The probability of risk may be determined directly from the value of the RI or may be the value of the RI. Additionally, the RI value may be displayed in combination with the regions (not shown), for example, in the regions or in an associated legend.

Figure 9:
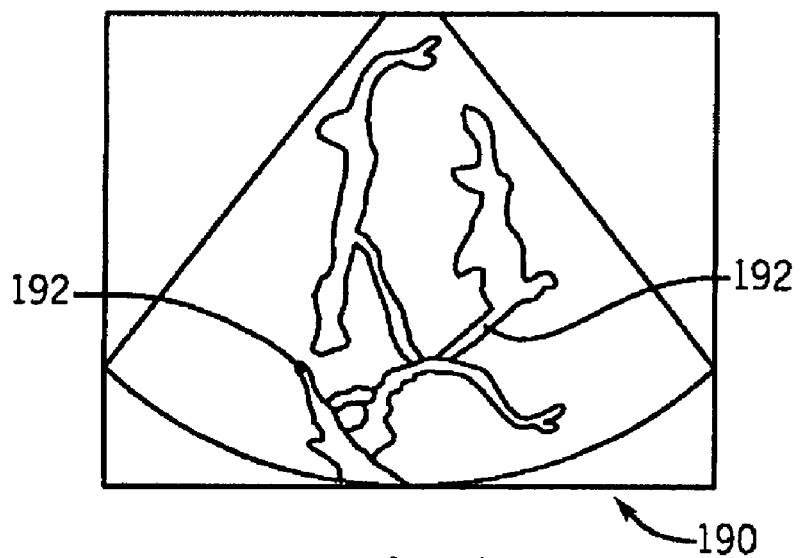
FIG. 9 is an ultrasound image that includes identified regions overlaid on the image indicating a probability of remodeling in accordance with various embodiments of the invention.

However, the various embodiments are not limited to a particular type of display. For example, as shown in FIG. 9, an ultrasound image 190 may include identified regions 192 overlaid on the image indicating a probability of remodeling as described herein and which may be color coded as described above.

It should be noted that the various embodiments are not limited to predicting remodeling based on the indices described herein. The various embodiments may be implemented in connection with any ultrasound system wherein any parameter indicative of potential ischemia is extracted from the ultrasound data, for example, from one or more strain curves. This parameter then may be used to map a number (e.g., an index number) to the probability that a portion of the heart is going to die.

Figure 10:
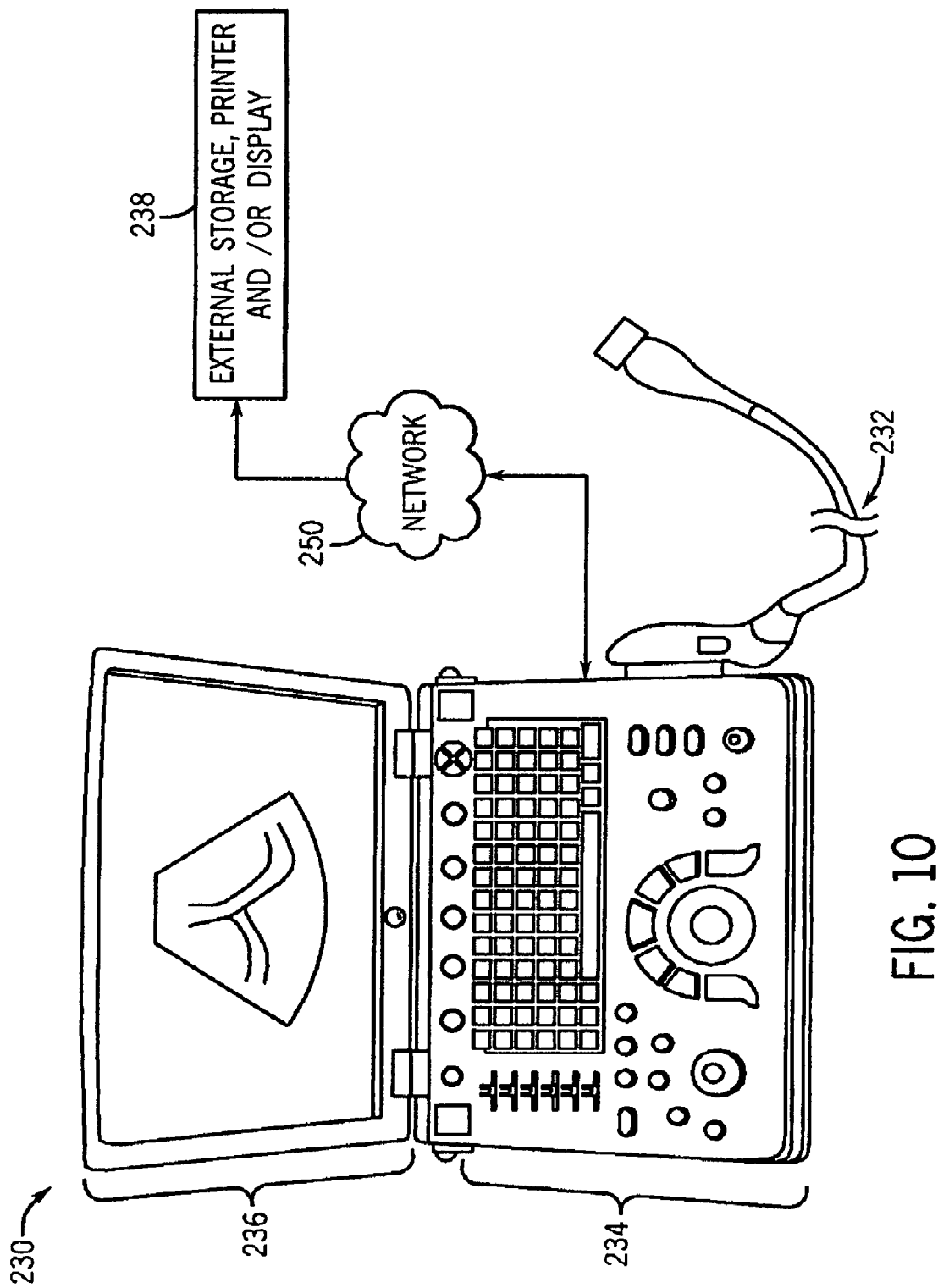
FIG. 10 is a drawing illustrating a miniaturized ultrasound imaging system that may be configured to determine a probability of remodeling in accordance with various embodiments of the invention.

It also should be noted that the various embodiments may be implemented in connection with different types and kinds of ultrasound systems. For example, as shown in FIG. 10, a 3D-capable miniaturized ultrasound imaging system 230 having a probe 232 may be provided. For example, the probe 232 may be a miniaturized probe as previously described above. A user interface 234 (that may also include an integrated display 236) is provided to receive commands from an operator. As used herein, "miniaturized" means with respect to the ultrasound system 230 that the system is a handheld or hand-carried device or is configured to be carried in a person's hand, pocket, briefcase-sized case, or backpack. For example, the ultrasound system 230 may be a hand-carried device having a size of a typical laptop computer, for instance, having dimensions of approximately 2.5 inches in depth, approximately 14 inches in width, and approximately 12 inches in height. The ultrasound system 230 may weigh about ten pounds, and thus is easily portable by the operator. The integrated display 236 (e.g., an internal display) is also provided and is configured to display a medical image.

The ultrasonic data may be sent to an external device 238 via a wired or wireless network 250 (or direct connection, for example, via a serial or parallel cable or USB port). In some embodiments, the external device 238 may be a computer or a workstation having a display. Alternatively, the external device 238 may be a separate external display or a printer capable of receiving image data from the hand carried ultrasound system 230 and of displaying or printing images that may have greater resolution than the integrated display 236.

Figure 11:
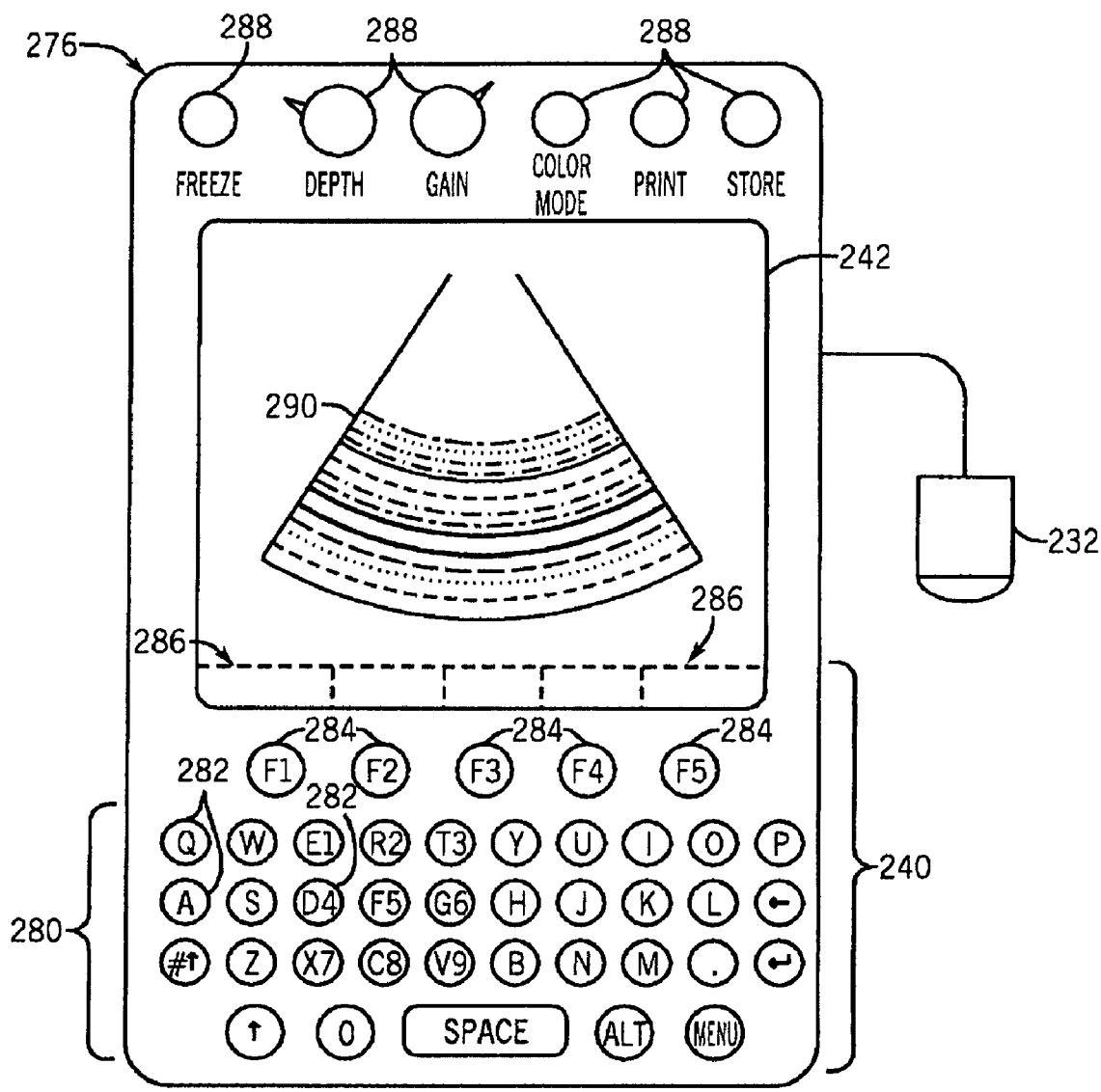
FIG. 11 is a drawing illustrating a hand carried or pocket-sized ultrasound imaging system that may be configured to a determine probability of remodeling in accordance with various embodiments of the invention.

As another example shown in FIG. 11, a hand carried or pocket-sized ultrasound imaging system 276 may be provided. In the system 276, display 242 and user interface 240 form a single unit. By way of example, the pocket-sized ultrasound imaging system 276 may be a pocket-sized or hand-sized ultrasound system approximately 2 inches wide, approximately 4 inches in length, and approximately 0.5 inches in depth and weighs less than 3 ounces. The display 242 may be, for example, a 320×320 pixel color LCD display (on which a medical image 290 may be displayed in combination with a graphical representation of the probe 232). A typewriter-like keyboard 280 of buttons 282 may optionally be included in the user interface 240. It should be noted that the various embodiments may be implemented in connection with a pocket-sized ultrasound system 276 having different dimensions, weights, and power consumption.

Multi-function controls 284 may each be assigned functions in accordance with the mode of system operation. Therefore, each of the multi-function controls 284 may be configured to provide a plurality of different actions. Label display areas 286 associated with the multi-function controls 284 may be included as necessary on the display 242. The system 276 may also have additional keys and/or controls 288 for special purpose functions, which may include, but are not limited to "freeze," "depth control," "gain control," "color-mode," "print," and "store."

Figure 12:
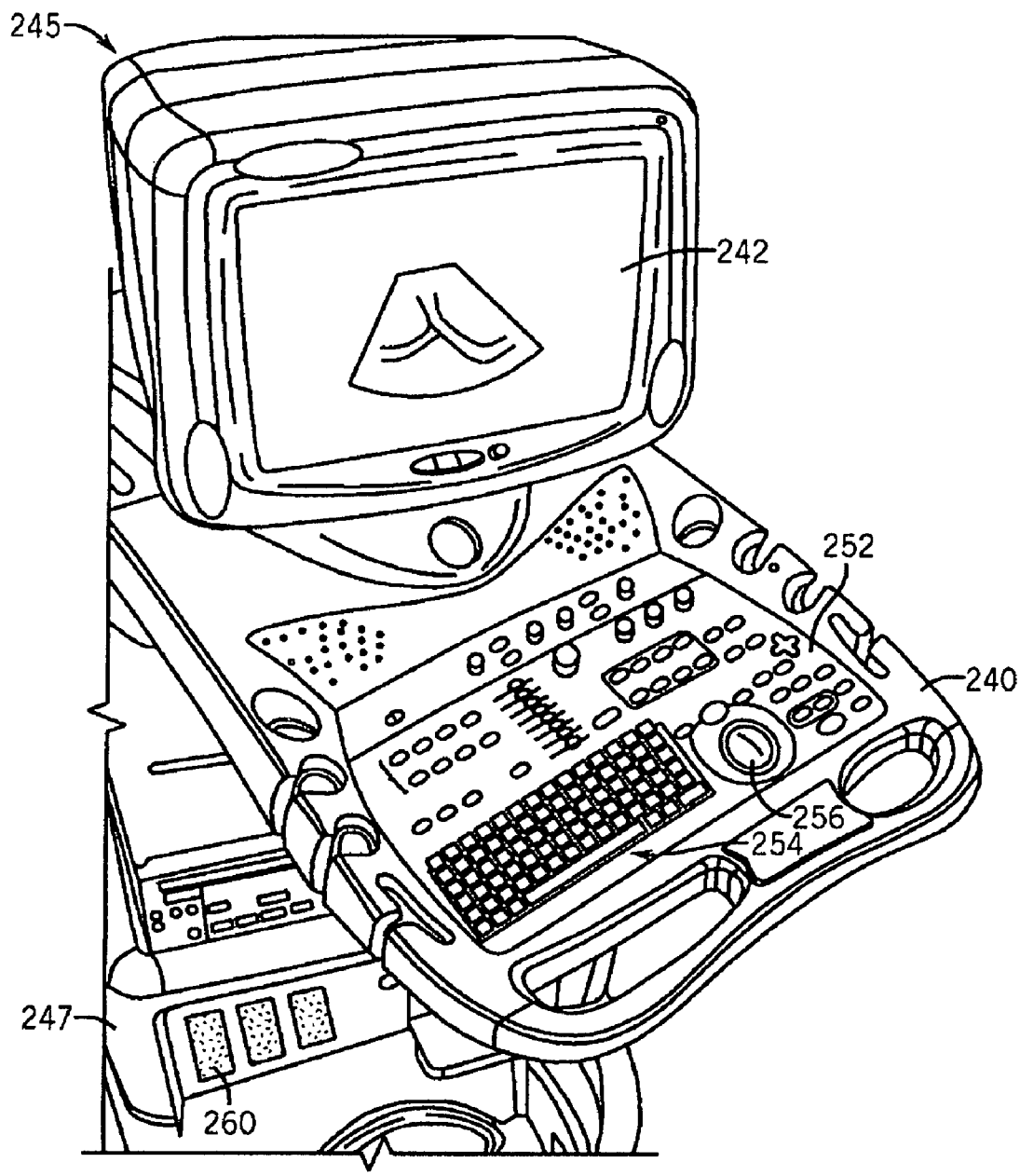
FIG. 12 is a drawing illustrating a console-based ultrasound imaging system provided on a movable base that may be configured to determine a probability of remodeling in accordance with various embodiments of the invention.

As another example shown in FIG. 12, a console-based ultrasound imaging system 245 may be provided on a movable base 247. The portable ultrasound imaging system 245 may also be referred to as a cart-based system. A display 242 and user interface 240 are provided and it should be understood that the display 242 may be separate or separable from the user interface 240. The user interface 240 may optionally be a touchscreen, allowing the operator to select options by touching displayed graphics, icons, and the like.

The user interface 240 also includes control buttons 252 that may be used to control the portable ultrasound imaging system 245 as desired or needed, and/or as typically provided. The user interface 240 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 254 and trackball 256 may be provided. The system 245 has at least one probe port 260 for accepting probes.

Figure 13:
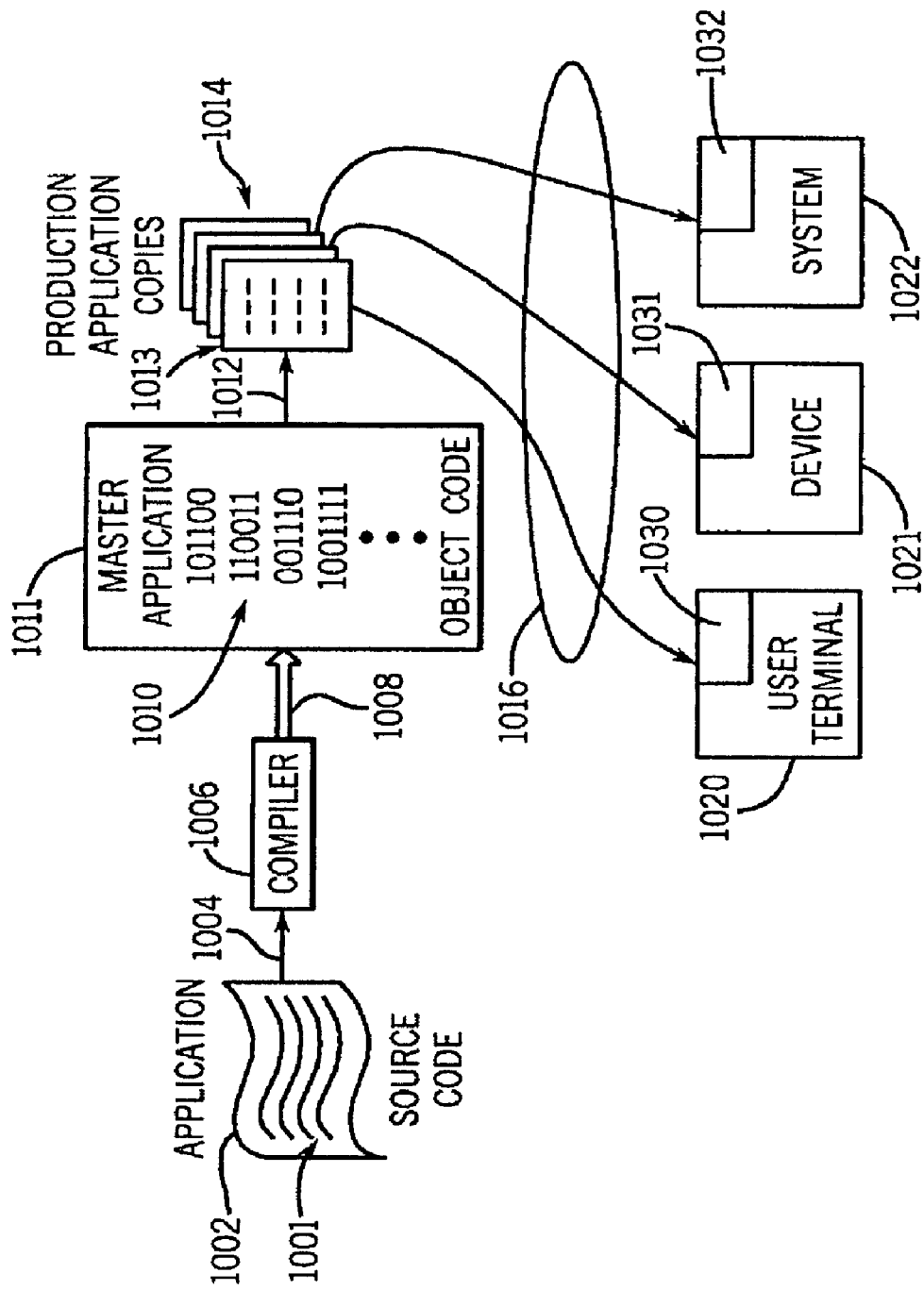
FIG. 13 is a block diagram of exemplary manners in which embodiments of the invention may be stored, distributed and installed on computer readable medium.

FIG. 13 is a block diagram of exemplary manners in which embodiments of the present invention may be stored, distributed and installed on computer readable medium. In FIG. 13, the "application" represents one or more of the methods and process operations discussed above.

As shown in FIG. 13, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous times, as denoted by path 1012, to produce production application copies 1013 that are saved on separate production computer readable medium 1014. The production computer readable medium 1014 is then conveyed, as denoted by path 1016, to various systems, devices, terminals and the like. In the example of FIG. 13, a user terminal 1020, a device 1021 and a system 1022 are shown as examples of hardware components, on which the production computer readable medium 1014 are installed as applications (as denoted by 1030-1032).

The source code may be written as scripts, or in any high-level or low-level language. Examples of the source, master, and production computer readable medium 1002, 1011 and 1014 include, but are not limited to, CDROM, RAM, ROM, Flash memory, RAID drives, memory on a computer system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011 or 1014 between two geographic locations. The paths 1004, 1008, 1012 and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, inter-continental and the like.

The operations noted in FIG. 13 may be performed in a widely distributed manner world-wide with only a portion thereof being performed in the United States. For example, the application source code 1001 may be written in the United States and saved on a source computer readable medium 1002 in the United States, but transported to another country (corresponding to path 1004) before compiling, copying and installation. Alternatively, the application source code 1001 may be written in or outside of the United States, compiled at a compiler 1006 located in the United States and saved on a master computer readable medium 1011 in the United States, but the object code 1010 transported to another country (corresponding to path 1012) before copying and installation. Alternatively, the application source code 1001 and object code 1010 may be produced in or outside of the United States, but production application copies 1013 produced in or conveyed to the United States (e.g. as part of a staging operation) before the production application copies 1013 are installed on user terminals 1020, devices 1021, and/or systems 1022 located in or outside the United States as applications 1030-1032.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

The various embodiments and/or components, for example, the ultrasound system, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining a likelihood of myocardial remodeling, the method comprising:
    obtaining ultrasound information relating to a heart;
    calculating a local work of the heart using the ultrasound information acquired by an ultrasound system;
    determining, from the calculated local work, remodeling index (RI) values for each of a plurality of local regions of the heart; and
    determining a likelihood of myocardial remodeling of the heart based on the RI values.

2. A method in accordance with claim 1 wherein determining a likelihood of myocardial remodeling comprises predicting a probability of myocardial remodeling.

3. A method in accordance with claim 1 further comprising obtaining regional measurements using the ultrasound information.

4. A method in accordance with claim 3 wherein the regional measurements comprise local myocardial strain measurements.

5. A method in accordance with claim 3 wherein the regional measurements comprise the calculated local work.

6. A method in accordance with claim 1 further comprising mapping the likelihood of myocardial remodeling.

7. A method in accordance with claim 6 wherein the mapping comprises generating a bullseye plot.

8. A method in accordance with claim 1 wherein calculating the local work of the heart further comprises determining post-systolic shortening index (PSSI) values.

9. A method in accordance with claim 1 wherein calculating the local work of the heart further comprises determining segmental work (SW) values.

10. A method in accordance with claim 1 wherein the RI values are based on a recruitment time.

11. A method in accordance with claim 1 wherein the RI values are based on a local myocardial strain value.

12. A method in accordance with claim 1 wherein determining a likelihood of myocardial remodeling comprises predicting a regional probability of myocardial remodeling.

13. A method in accordance with claim 1 wherein determining a likelihood of myocardial remodeling comprises predicting a global probability of myocardial remodeling.

14. A method in accordance with claim 1 wherein obtaining ultrasound information comprises obtaining at least three ultrasound views of the heart.

15. A method in accordance with claim 1 wherein determining the likelihood of myocardial remodeling comprises determining after a myocardial infarction the likelihood of myocardial remodeling based on a remodeling cascade, wherein the remodeling cascade comprises systolic impairment secondary to a continuous loss of contractile material, resulting in an increased end-systolic volume, an increased cardiac size, and a secondary augmentation of a diastolic filling pressure and cardiac distensibility.

16. A method in accordance with claim 1 wherein determining the likelihood of myocardial remodeling of the heart comprises modeling of ventricular remodeling after myocardial infarction.

17. A method in accordance with claim 1 wherein determining the likelihood of myocardial remodeling of the heart based on the calculated local work of the heart comprises determining a change in a length of heart muscle at one or more local regions of the heart from a start of heart contraction to an end of the heart contraction.

18. A method in accordance with claim 1 further comprising determining the RI values using a strain map to identify heart areas having an increased after load resulting from an infracted area of the heart.

19. A method for determining a likelihood of myocardial remodeling, the method comprising:
- determining a plurality of strain curves over time based on ultrasound information of a heart acquired by an ultrasound system;
- determining an amount of local work for each point in a left ventricle of the heart based on the strain curves;
- determining, from the amount of local work, remodeling index (RI) values for each of a plurality of local regions of the heart;
- generating a remodeling map based on the determined RI values, the remodeling map including regions indicative of possible myocardial remodeling; and
- determining a likelihood of regional myocardial remodeling based on the remodeling map.

20. A method in accordance with claim 19 wherein local work comprises mechanical myocardial function.

21. A method in accordance with claim 19 wherein the remodeling map is color coded to indicate different levels of likelihood of myocardial remodeling.

22. An ultrasound system comprising:
- a transducer configured to acquire ultrasound information of a heart; and a processor module configured to (i) calculate a local work of the heart using the ultrasound information, (ii) determine, from the calculated local work, remodeling index (RI) values for each of a plurality of local regions of the heart, and (iii) determine a likelihood of myocardial remodeling of the heart based on the RI values.

* * * * *